(12) United States Patent
Turos et al.

(10) Patent No.: US 6,476,015 B1
(45) Date of Patent: Nov. 5, 2002

(54) N-THIOLATED β-LACTAM ANTIBIOTICS

(75) Inventors: Edward Turos, Temple Terrace; Edward T. Carpenter, Tampa; Timothy Long, Tampa; Daniel V. Lim, Tampa; Sonja S. Dickey, Tampa, all of FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/621,646

(22) Filed: Jul. 24, 2000

Related U.S. Application Data

(60) Provisional application No. 60/145,004, filed on Jul. 22, 1999.

(51) Int. Cl.[7] .................. A61K 31/397; A61P 31/04; C07D 205/06
(52) U.S. Cl. ................... 514/210.15; 540/355
(58) Field of Search ............... 514/210.15; 540/355

(56) References Cited

PUBLICATIONS

Hawley, Gessner, "The Condensed Chemical Dictonary", 1997, Van Nostrand, New York, p. 498.*
John D. Roberts and Marjorie C. Caserio, "Basic Principles of Organic Chemistry", Benjamin, New York, 1964, p 529.*
Ren, Xiao–Feng; Konaklieva, Monika I.; Shi, Hongchang; Dickey, Sonja; Lim, Daniel V.; Gonzalez, Javier; Turos, Edward, J. Org. Chem., 63(24), 8898–8917, 1998.*
Burnett, Duane A.; Hart David, J.; Liu, Jun, J. Org. Chem., 51(10), 1929–30 (English) 1986.*
"Synthesis of a Novel Carbapenem–Potassium (5R,6R)–1, 1–Difluoro–2–Phenyl–6–(1R–Hydroxyethyl)–Carbapen–2EM–3–Carboxylate. The Use of New N–Protecting Group in a β–Lactam Synthesis," Nalini V. Shah and Lovji D. Cama, *Heterocycles*, vol. 25, 1987.

* cited by examiner

*Primary Examiner*—Mukund J. Shah
*Assistant Examiner*—Thomas C McKenzie
(74) *Attorney, Agent, or Firm*—Saliwanchik, Lloyd & Saliwanchik

(57) ABSTRACT

Substituted monocyclic β-lactam compounds that are N-1-thiolated monolactams, and which exhibit wide-ranging antibacterial activities, having a single 4-membered azetidinone ring in which: the N-1 nitrogen atom of the azetidinone ring is bonded to sulfur but is not sulfonated, of the formula:

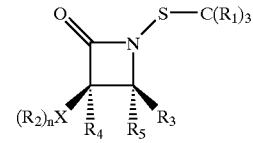

wherein $R_{1-5}$ are independently hydrogen, alkyl, heteroalkyl, aryl, heteroaryl, alkenyl, or alkynyl; X is H, C, or O; and n=0–3. Chemical synthesis of these compounds by a [2+2]-imine-acid chloride cycloaddition, and methods for subsequent derivatization, are also disclosed. The compounds and compositions disclosed herein are useful as antibacterial and antibiotic agents.

20 Claims, No Drawings

N-THIOLATED β-LACTAM ANTIBIOTICS

RELATED APPLICATIONS

The present application claims priority from U.S. Provisional Application No. 60/145,004, filed Jul. 22, 1999, which is hereby incorporated in its entirety by reference.

FIELD OF THE INVENTION

This invention relates to a novel class of monocyclic β-lactam compounds and compositions comprising a single, 4-membered azetidinone ring, which exhibit wide-ranging antibacterial activity, wherein the $N_1$ nitrogen atom of the azetidinone ring is bonded to sulfur but is not sulfonated. Specifically, compounds are disclosed that inhibit growth of diverse strains of bacteria wherein substitutions at positions $C_3$ and $C_4$ of the azetidinone ring, and at the sulfur atom, produce antibacterial agents of varying bacterial specificity and efficacy. Additionally, the invention relates to methods for the synthesis of the aforementioned compounds.

BACKGROUND OF THE INVENTION

The clinical use of antibiotics in the $20^{th}$ century has substantially decreased morbidity from bacterial infections. The early success of penicillin was extended by various sulfonamide drugs developed in the 1930s, and subsequently by a "golden" period of discovery, between 1945 and 1970, during which a wide array of highly effective agents were discovered and developed. See: Chopra, I., Hodgson, J., Metcalf, B. & Poste, G. "The Search for Antimicrobial Agents Effective against Bacteria Resistant to Multiple Antibiotics" (1997) *Antimicrobial Agents and Chemotherapy* 41:497–503.

However, since the 1980s the introduction of new antibiotics has slowed, and, concurrently, there has been an alarming increase in bacterial resistance to existing agents that now constitutes a serious threat to public health. See: Brown, A. G. (1987) "Discovery and Development of New β-Lactum Antibiotics" *Pure & Appl. Chem.* 59:475–484. Hospitals, nursing homes and infant day care centers have become breeding grounds for the most tenacious drug-resistant pathogens. See: "Frontiers in Biotechnology" (1994) *Science* 264:359–393. There has been an alarming rise in drug resistant staphylococci, enterococci, streptococci, and pneumococci infections, and an increase in tuberculosis, influenza and sepsis.

For several decades, β-lactam antibiotics have been widely used to control bacterial infections. Since the discovery of penicillin, countless numbers of analogues have been prepared and tested (see for example: U.S. Pat. No. 5,142,039 to Blaszczak et al., and U.S. Pat. No. 5,338,861 to Botts et al.), and a variety of successful modifications have been made to the five-membered ring, including (1) replacement of the sulfur atom with carbon or oxygen, (2) oxidation of the sulfur to the sulfoxide or sulfone, (3) enlargement to a larger ring, (4) incorporation of unsaturation, (5) attachment of additional fused rings, and (6) removal of the five membered ring. As a result, new β-lactam ring systems have been introduced, including the penems, cephalosporins, carbapenems, oxapenems, oxacephams, as well as monocyclic, spirocyclic, and multicyclic β-lactams. In the case of monocyclic β-lactams (see: Sykes, R. B., Cimarusti, C. M., Bonner, D. P., Bush, K., Floyd, D. M., Georgopapadakou, N. H., Koster, W. H., Trejo, W. H. & Wells, J. S. (1981) "Monocyclic β-Lactam Antibiotics Produced by Bacteria" *Nature* 291:489–490), which directly relates to the present invention, removal of the five-membered ring leaves a four-membered β-lactam ring, the structural core of which is 2-azetidinone (1):

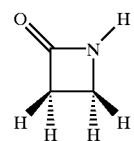

Monocyclic antibiotics successfully developed by derivatization of this core structure include the monobactams (see: Slusarchyk, W. A., Dejneka, T., Gordon, E. M., Weaver, E. R. & Koster, W. H. "Monobactams: Ring Activating N-1-Substituents in Monocyclic β-Lactam Antibiotics" (1984) *Heterocycles* 21:191–209.), which have 2-oxoazetidine sulfonic acid as their characteristic structure. A key feature of the monobactams is the activation of the β-lactam ring towards nucleophilic attack by bacterial transpeptidases that is caused by the electron-withdrawing potential of the sulfonated nitrogen atom. Alternative activating groups for monobactam derivatives have been discovered, including phosphate, phosphonate, and analogues in which a spacer atom is interposed between the ring nitrogen and activating group (see: Breuer, H., Straub, H., Treuner, U. D., Drossard, J.-M., Höhn, H. & Lindner, K. R. "[(2-oxo-1-azetidinyl)oxy] acetic acids: a new class of synthetic monobactams" (1985) *J. Antibiotics* 38:813–818, and Slusarchyk, W. A., Dejneka, T., Gordon, E. M., Weaver, E. R. & Koster, W. H. "Monobactams: Ring Activating N-1-Substituents in Monocyclic β-Lactam Antibiotics" (1984) *Heterocycles* 21:191–209).

The primary targets of β-lactams are the penicillin binding proteins, a group of bacterial proteins that mediate the final step of bacterial cell wall biosynthesis in which a terminal alanine-alanine linkage of a peptidoglycan strand is cleaved by an active site serine and crosslinked to another peptidoglycan fragment, thus strengthening the bacterial cell wall. Penicillin interrupts this crosslinking step by acylating the serine with its reactive β-lactam ring. Following acylation, ring opening results in further chemical fragmentations that are deleterious to the enzyme. Also among the penicillin binding proteins are the β-lactamases: enzymes that degrade β-lactams. Clavulinic acid targets these enzymes, and is therefore useful in conjunction with established penicillins in combination therapies for combating certain resistant strains of bacteria. See: Chopra, I., Hodgson, J., Metcalf, B. & Poste, G. "The Search for Antimicrobial Agents Effective against Bacteria Resistant to Multiple Antibiotics" (1997) *Antimicrobial Agents and Chemotherapy* 41:497–503.

There is a clear need for new antibacterial agents to combat pathogenic bacteria that have become resistant to current antibiotics. Towards this end, a novel class of derivatized, N-thiolated, monocyclic β-lactams have been developed in the present invention, that exhibit strong antibacterial activity against a wide variety of species and strains.

SUMMARY OF THE INVENTION

The invention comprises a novel class of monocyclic β-lactam antibacterial and antibiotic agents, herein termed N-1 thiolated monolactams, of the general structure:

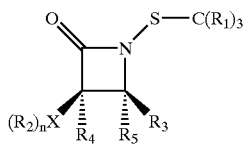

(2)

independently hydrogen, alkyl, heteroalkyl, aryl, heteroaryl, alkenyl, or alkynyl; X is H, C or O; and n=0 to 3.

It is an object of the present invention to provide these compounds, including their salts, hydrates, and in combinations with suitable pharmaceutical carriers, as antibacterial and antibiotic agents.

It is a further object of this invention to provide such compounds, wherein $R_4$ and $R_5$ are hydrogen, and —$C(R_1)_3$ is methyl or benzyl (—$CH_2Ph$).

It is yet a further object of the invention to provide antibacterial and antibiotic agents with varying bacterial strain specificities and efficacies, by the expedient means of varying substituents of the 2-azetidinone ring, including but not limited to nitrogen (N-1) thiomethyl or thiobenzyl moieties, and substitutions at the $C_3$ and $C_4$ positions.

In another embodiment, it is a further object of this invention to provide methods for inhibiting the growth of bacteria by administering the compounds of the present invention, and to provide methods for the treatment of bacterial infections of a patient, in which one or more doses of an effective amount of the compounds and compositions of the present invention are administered to a patient.

It is yet a further objective of the present invention to provide compounds and compositions suitable for the treatment of gonorrhea.

The present invention confers numerous advantages over the compounds of the prior art, including the following: ease of synthesis, whereby compounds with diverse substituents may be synthesized and tested for antibacterial and antibiotic activity; the invention provides novel antibacterial and antibiotic agents to which bacterial pathogens have not yet acquired resistance; and the invention provides novel compounds for the treatment of increasingly common and resistant diseases such as gonorrhea. Surprisingly, the inventors have found that antibacterial and antibiotic activities can be obtained in compounds that do not possess traditional activating groups attached to the sulfur, as required for activity in conventional monobactams which contain, for example, sulfone groups. The inventors have also surprisingly discovered that derivatization of structure (2) at the positions indicated by the $R_{1-5}$ and X, results in compounds exhibiting different specificities for different bacterial pathogens, in a manner that is currently not possible to predict a priori. This aspect is therefore an unobvious benefit of the present invention. The present invention fullfills a dire need in that novel antibacterial compounds are urgently required as bacterial pathogens increasingly acquire immunity towards the present arsenal of antibiotics.

DETAILED DESCRIPTION OF THE INVENTION

The term "N-1 thiolated monolactam" is used herein to refer to a monocyclic 4-membered beta-lactam compound comprising an 4-azetidinone ring in which the ring nitrogen (N-1) atom is covalently bonded to a sulfur that is covalently bonded to a carbon-centered moiety, and which may be further modified as described herein. Specifically, referring now to compound (2), X may be a hydrogen (in which case, n is preferably zero), or a carbon atom (in which case n is preferably 3), or an oxygen atom (in which case, n is preferably 1), and $R_2$ may be any substituent as herein defined. Similarly, $R_1$ and $R_{3-5}$ may be independently any substituent as herein defined except that the compounds 1-thiomethyl-3-methoxy-4-phenylethynyl-2-oxoazetidine and 1-thiomethyl-3-methoxy-4-(O-acetyl)phenylethynyl-2-oxoazetidine are specifically excluded from the definition of N-1 thiolated monolactam as used herein.

Thus, in preferred embodiments, $R_1$ is hydrogen or benzyl, and in most preferred embodiments $R_1$ is hydrogen. Substituents comprising —$X(R_2)_n$ are preferably methoxy and hydrogen, and most preferably methoxy. $R_3$ may be alkyl, heteroalkyl, aryl, heteroaryl, alkenyl, or alkynyl. Preferred $R_3$ substituents are phenylethynyl, acetoxy, 1-propenyl, ortho-chlorophenyl, ortho-nitrophenyl, 2-thiophene, or S,S-dioxo-thiophene. $R_4$ and $R_5$ may be independently alkyl, heteroalkyl, aryl, heteroaryl, alkenyl, or alkynyl groups. In preferred embodiments, $R_4$ and $R_5$ are H.

The following definitions are used, unless otherwise described. Halo is fluoro, chloro, bromo, or iodo. "Alkyl," "alkoxy," etc. denote both straight and branched groups; but reference to an individual radical such as "propyl" embraces only the straight chain radical, a branched chain isomer such as "isopropyl" being specifically referred to. "Aryl" denotes a phenyl radical or an ortho-fused bicyclic carbocyclic radical having about nine to ten ring atoms in which at least one ring is aromatic. "Heteroaryl" encompasses a radical attached via a ring carbon of a monocyclic aromatic ring containing five or six ring atoms consisting of carbon and one to four heteroatoms each selected from the group consisting of non-peroxide oxygen, sulfur, and $N(R_x)$ wherein $R_x$ is absent or is hydrogen, oxo, alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having one or more chiral center(s) may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis, from optically-active starting materials. by chiral synthesis, or by chromatographic separation using a chiral stationary phase), and how to determine antibacterial activity using the tests described herein, or using other tests which are well known in the art. The preferred absolute configuration for compounds of the invention is that shown in formula (2) above.

Specific and preferred values listed below for radicals, substituents, and ranges, are for illustration only; they do not exclude other defined values or other values within defined ranges for the radicals and substituents.

Specifically, "alkyl" can include methyl, ethyl, propyl, isopropyl, butyl, iso-butyl, sec-butyl, pentyl, 3-pentyl, hexyl, heptyl, octyl, nonyl, decyl, undecyl, dodecyl, tridecyl, tetradecyl or pentadecyl; "alkenyl" can include vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl; 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, 1-tridecenyl, 2-tridecenyl, 3-tridecenyl, 4-tridecenyl, 5-tridecenyl, 6-tridecenyl, 7-tridecenyl, 8-tridecenyl, 9-tridecenyl, 10-tridecenyl, 11-tridecenyl, 12-tridecenyl, 1-tetradecenyl, 2-tetradecenyl, 3-tetradecenyl, 4-tetradecenyl, 5-tetradecenyl, 6-tetradecenyl 7-tetradecenyl, 8-tetradecenyl, 9-tetradecenyl, 10-tetradecenyl, 11-tetradecenyl, 12-tetradecenyl, 13-tetradecenyl, 1-pentadecenyl, 2-pentadecenyl, 3-pentadecenyl, 4-pentadecenyl, 5-pentadecenyl, 6-pentadecenyl, 7-pentadecenyl, 8-pentadecenyl, 9-pentadecenyl, 10-pentadecenyl, 11-pentadecenyl, 12-pentadecenyl, 13-pentadecenyl, 14-pentadecenyl; "alkoxy" can include methoxy, ethoxy, propoxy, isopropoxy, butoxy, iso-butoxy, sec-butoxy, pentoxy, 3-pentoxy, hexoxy, heptyloxy, octyloxy, nonyloxy, decyloxy, undecyloxy, dodecyloxy, tridecyloxy, tetradecyloxy, or pentadecyloxy; "alkanoyl" can include acetyl, propanoyl, butanoyl, pentanoyl, hexanoyl, heptanoyl, octanoyl, nonanoyl, decanoyl, undecanoyl, dodecanoyl, tridecanoyl, tetradecanoyl, or pentadecanoyl; "cycloalkyl" can include cyclopropyl, cyclobutyl, cyclopentyl, cyclohexyl, cycloheptyl, or cyclooctyl. "Aryl" can include phenyl, indenyl, 5,6,7,8-tetrahydronaphthyl, or naphthyl. "Heteroaryl" can include furyl, imidazolyl, tetrazolyl, pyridyl, (or its N-oxide), thienyl, pyrimidinyl (or its N-oxide), indolyl, or quinolyl (or its N-oxide).

Specific independent values for $R_{1-5}$, include alkyl, alkenyl, alkynyl, cycloalkyl, cycloalkyl($C_1$–$C_{10}$)alkyl, ($C_3$–$C_8$)cycloalkyl($C_1$–$C_{15}$)alkenyl, ($C_3$–$C_8$)cycloalkyl ($C_1$–$C_{15}$)alkynyl, ($C_1$–$C_{15}$)alkoxy, ($C_1$–$C_{15}$)alkanoyl, or ($C_1$–$C_{15}$)alkanoyloxy; wherein $R^1$ is optionally substituted with one or more (e.g. 1, 2, 3, or 4) substituents independently selected from the group consisting of halo, nitro, cyano, hydroxy, trifluoromethyl, trifluoromethoxy, ($C_1$–$C_{15}$) alkyl, ($C_2$–$C_{15}$)alkenyl, ($C_2$–$C_{15}$)alkynyl, ($C_3$–$C_8$) cycloalkyl, ($C_3$–$C_8$)cycloalkyl ($C_1$–$C_{15}$)alkyl, ($C_3$–$C_8$) cycloalkyl($C_2$–$C_{15}$)alkenyl, ($C_3$–$C_8$)cycloalkyl($C_2$–$C_{15}$) alkynyl, ($C_1$–$C_{15}$)alkoxy, ($C_{1-C15}$)alkanoyl, ($C_1$–$C_{15}$) alkanoyloxy, C(=O)OR$_a$, C(=O)NR$_b$ R$_c$, OC(=O) OR$_a$, OC(=O) NR$_b$ R$_c$, and NR$_e$ R$_f$.

Another specific value for $R_{1-5}$, includes aryl optionally substituted with 1, 2, or 3 substituents independently selected from the group consisting of halo, nitro, cyano, hydroxy, trifluoromethyl, trifluoromethoxy, ($C_1$–$C_6$)alkyl, ($C_2$–$C_{10}$)alkenyl, ($C_2$–$C_{10}$)alkynyl, ($C_3$–$C_8$)cycloalkyl, ($C_3$–$C_8$)cycloalkyl ($C_1$–$C_6$)alkyl, ($C_1$–$C_{10}$)alkoxy, ($C_1$–$C_{10}$) alkanoyl, ($C_2$–$C_{10}$)alkanoyloxy, C(=O)OR$_a$, C(=O)NR$_b$ R$_c$, or NR$_e$ R$_f$.

Other specific values for $R_{1-5}$, include independently phenyl or naphthyl, optionally substituted with a substituent selected from the group consisting of halo, nitro, cyano, hydroxy, trifluoromethyl, trifluoromethoxy, ($C_1$–$C_6$)alkyl, ($C_2$–$C_{10}$)alkenyl, ($C_2$–$C_{10}$)alkynyl, ($C_3$–$C_8$)cycloalkyl, ($C_3$–$C_8$)cycloalkyl($C_1$–$C_6$)alkyl, ($C_1$–$C_{10}$)alkoxy, ($C_1$–$C_{10}$) alkanoyl, ($C_2$–$C_{10}$)alkanoyloxy, C(=O)OR$_a$, C(=O)NR$_b$ R$_c$, or NR$_e$ R$_f$.

Still other specific values for $R_{1-5}$, include aryl, heteroaryl, aryl($C_1$–$C_6$)alkyl, heteroaryl($C_1$–$C_6$)alkyl, aryl ($C_2$–$C_6$)alkenyl, heteroaryl($C_2$–$C_6$)alkenyl, aryl($C_2$–$C_6$) alkynyl, or heteroaryl($C_2$–$C_6$)alkynyl; wherein any aryl or heteroaryl is optionally substituted with halo, nitro, cyano, hydroxy, trifluoromethyl, trifluoromethoxy, ($C_1$–$C_{15}$)alkyl, ($C_2$–$C_{15}$)alkenyl, ($C_2$–$C_{15}$)alkynyl, ($C_3$–$C_8$)cycloalkyl, ($C_3$–$C_8$)cycloalkyl($C_1$–$C_{15}$)alkyl, ($C_3$–$C_8$)cycloalkyl— ($C_2$–$C_{15}$)alkenyl, $C_3$–$C_8$)cycloalkyl($C_2$–$C_{15}$)alkynyl, ($C_1$–$C_{15}$)alkoxy, ($C_1$–$C_{15}$)alkanoyl, ($C_1$–$C_{15}$)alkanoyloxy, C(=O)OR$_a$, C(=O)NR$_b$ R$_c$, or NR$_e$ R$_f$.

The compounds of the present invention exhibit broad antibacterial activity against several families of bacteria in the Gram-negative and Gram-positive range, and against beta-lactamase producing strains. Because of their powerful antibacterial properties, the present compounds may also be used to supplement feed for animals.

In addition, the compounds of the present invention that exhibit antibacterial activity may also be used as medicaments, and also as substances for preserving inorganic and organic materials, especially organic materials of all kinds, for example polymers, lubricants, paints, fibers, leather, paper, timber, foodstuffs, and water.

The compounds of the present invention may also be used to prevent, alleviate, or cure diseases caused by pathogens whose growth is inhibited by these compounds. The instant compounds are particularly active against bacteria and bacteria-like microorganisms. They are therefore suitable for use in human and veterinary medicine, for the prophylaxis and chemotherapy of local and systemic infections caused by these pathogens.

As an illustrative, but not limiting, list of pathogens, the following pathogenic microorganisms are possible targets of the compounds of the present invention. Micrococcaceae, such as Staphylococci, for example *Staphylococcus aureus, Staph. epidermidis* and *Staph. aerogenes*; Lactobacteriaceae, such as Streptococci, for example *Streptococcus pyogenes*; Neisseriaceae, such as Neisseriae, for example *Neisseria gonorrhoeae* (Gonococci); Corynebacteriaceae, such as Corynebacteria; Listeria bacteria; Erysipelothrix bacteria; Kurthia bacteria; Enterobacteriaceae, such as Escherichia bacteria of the Coli group; Klebsiella bacteria; Erwiniae; Serratia; Proteae bacteria; Providencia bacteria; Salmonella bacteria; Shigella; Pseudomonadaceae; Aeromonas bacteria; Spirillaceae, such as Vibrio bacteria; Spirillum bacteria; Parvobacteriaseae; Brucella bacteria; Bordetella bacteria; Moraxella bacteria; Fusiform bacteria; Bacillaceae; Clostridia; Spirochaetaceae; Treponema bacteria; and Leptospira bacteria.

Examples which may be cited of diseases which can be prevented, alleviated, or cured by the compounds of the present invention are: diseases of the respiratory passages and of the pharyngeal cavity; otitis; pharyngitis; pneumonia; peritonitis; pyelonephritis; cystitis; endocarditis; systemic infections; and bronchitis.

The compounds of the present invention include all hydrates and salts that can be prepared by those of skill in the art. Under conditions where the compounds of the present invention are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the present invention can be formulated as pharmaceutical compositions and administered to a patient, such as a human patient, in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its slats can be prepared in water or other suitable solvent, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure-form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula (I) in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

Accordingly, the invention includes a pharmaceutical composition comprising a compound of the present invention as described above; or a pharmaceutically acceptable salt thereof, in combination with a pharmaceutically acceptable carrier. Pharmaceutical compositions adapted for oral, topical or parenteral administration, comprising an amount of one or more compounds effective to treat a bacterial infection, are a preferred embodiment of the invention.

The present invention provides a novel class of monocyclic substituted β-lactams, specifically termed N-1 thiolated monolactams as defined herein. The present invention will therefore be fully understood by one of skill in the art by reference to the following embodiments, examples, and claims.

EXAMPLE 1

Monocyclic β-lactam (3) was synthesized according to the procedure given in Ren, X.-F., Konaklieva, M. I., Shi, H., Dickey, S., Lim, D. V., Gonzalez, J. & Turos, E. "Studies on Nonconventionally Fused Bicyclic β-Lactams" (1998) *J. Org. Chem.* 63:8898–8917, which is incorporated herein by reference, and discloses the synthetic methods that are used to prepare all β-lactam analogues herein. It will be apparent to one skilled in the art in the field of the present invention how the starting compounds and procedures below may be easily modified to produce other desired compounds, both those described herein, and others.

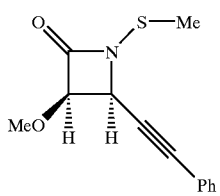

(3)

The following general experimental procedures were employed. All air- or moisture-sensitive procedures were performed under an argon atmosphere using glassware and syringes that were pre-dried in an oven overnight at 120 °C., and assembled while still hot. The imines were prepared by heating equimolar amounts of the appropriate aldehyde and amine in refluxing benzene solution in the presence of a small amount of p-toluenesulfonic acid under Dean-Stark conditions, followed by filtering the cooled solution through an approximately one inch plug of silica gel to remove residual amine. The purity of the crude imine was checked by $^1$H NMR prior to use. The acid chlorides were synthesized according to standard protocols by heating the corresponding carboxylic acid in thionyl chloride, removing residual volatiles by distillation, and used without further purification. THF and Et$_2$O were distilled immediately prior to use from Na/benzophenone under argon, and CH$_2$Cl$_2$ was freshly distilled from CaH$_2$ under N$_2$. Reactions were followed by TLC with fluorescence indicator (SiO$_2$-60, F-254) or 1% aqueous KMnO$_4$ stain. Flash chromatography was performed using 40 μm silica gel. $^1$H NMR spectra were recorded at 300, 360, 400 or 500 MHz and $^{13}$C NMR spectra were obtained at 75, 100, or 125 MHz. IR spectra were obtained as a thin film smeared onto NaCl plates. Melting points are uncorrected. Mass spectra were run using electron impact or chemical ionization methods.

Synthesis of N-thiolated β-lactam antibiotics

Formation of the azetidinone ring was performed by a [2+2]-imine-acid chloride cycloaddition, see: Staudinger, M. (1907) *Liebigs Ann. Chem.* 356:51, Georg, G. I. & Ravikumar, V. T. (1993) in: "The Organic Chemistry of β-Lactams", Verlag Chemie: New York, pp.295–368.

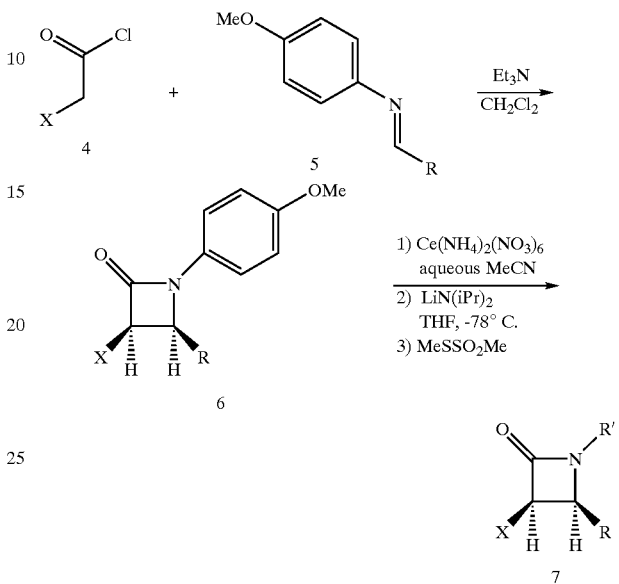

Procedure for the Preparation of N-aryl Protected β-lactams

To a stirred solution of Et$_3$N (1.25 mL, 9.0 mmol) and imine (5, R=CCPh) (1.88 g, 8.0 mmol) in CH$_2$Cl$_2$ (75 mL) at room temperature is added via cannula a solution of methoxyacetyl chloride (4, X=OMe) (0.91 g, 10.0 mmol) in CH$_2$Cl$_2$ (20 mL). The reaction mixture is stirred at room temperature for 30 min, poured into 5% aqueous HCl (75 mL), and extracted with CH$_2$Cl$_2$ (3×50 mL). The combined organic layers are dried over MgSO$_4$, filtered, and evaporated to give a brown oil that slowly crystallizes upon standing. Flash chromatography (2:1 CH$_2$Cl$_2$:hexanes and then CH$_2$Cl$_2$) of the crude material affords 2.2 g (89%) of β-lactam (6, X=OMe, R=CCPh): white solid; 116–117° C.; $^1$H NMR (400 MHz, CDCl$_3$) δ7.54–7.35 (m, 7H), 6.9 (d, J=7.8 Hz, 2H), 4.96 (d, J=4.8 Hz, 1H), 4.81 (d, J=4.8 Hz, 1H), 3.78 (s, 3H), 3.70 (s, 3H); $^{13}$C NMR (75 MHz, CDCl$_3$) δ163.1, 157.4, 132.6, 129.3, 129.2, 129.1, 128.8, 119.1, 115.0, 84.8, 81.7, 59.1, 56.1, 56.0, 50.3; IR (thin film) 1752 cm$^{-1}$ (β-lactam C=O). Anal. Calcd for C$_{19}$H$_{17}$NO$_3$: C, 74.25; H, 5.58; N, 4.56. Found: C, 74.10; H, 5.60; N, 4.57.

Procedure for the Dearylation of N-aryl β-lactams

To a solution of N-p-methoxyphenyl β-lactam (6, X=OMe, R=CCPh) (2.2 g, 7.2 mmol) in CH$_3$CN (100 mL) at 0° C. is added 100 mL of aqueous solution of ammonium cerium(IV) nitrate (11.8 g, 21.6 mmol) over 5 min. The reaction mixture is stirred for 25 min and then poured into aqueous 5% NaHSO$_3$ (100 mL), and the aqueous mixture is extracted with Et$_2$O (3×50 mL). The combined organic layers are treated with 5% NaHCO$_3$ (100 mL), and the aqueous layer is back-washed with one portion of diethyl ether (50 mL). The combined organic layers are dried over MgSO$_4$, filtered, and evaporated. Flash chromatography of the crude mixture affords 1.28 g (89%) of (7, X=OMe, R=CCPh, R'=H): white solid (mp 121–122°C.); 1H NMR (400 MHz, CDCl$_3$) δ7.42–7.35 (m, 5H), 6.80 (broad s, 1H), 4.72 (d, J=4.8 Hz, 1H), 4.60 (d, J=4.8 Hz, 1H), 3.60 (s, 3H);

$^{13}$C NMR (75 MHz, CDCl$_3$) δ167.5, 132.4, 129.4, 128.9, 122.7, 87.9, 87.1, 83.7, 58.8, 46.6; HRMS (CI, isobutane) calcd for C$_{12}$H$_{11}$NO$_2$ (M+1) 202.0865, obsd 202.0884. Anal. Calcd for C$_{12}$H$_{11}$NO$_2$: C, 71.63; H, 5.51; N, 6.96. Found: C, 71.55; H, 5.53; N, 6.91.

Procedure for the N-methylthiolation of β-lactams.

To a solution of (7, X=OMe, R=CCPh, R'=H) (1.28 g, 6.4 mmol) in THF at −78° C. is added n-butyllithium (5.0 mL, 1.38 M in hexanes, 6.9 mmol). After 30 minutes, methyl methanethiolsulfonate (0.85 g, 6.6 mmol) is added and the reaction mixture is stirred for 12 hours with warming to room temperature. The mixture is poured into 5% aqueous NH$_4$Cl (50 mL) and extracted with CH$_2$Cl$_2$ (3×50 mL). The combined organic layers are dried over MgSO$_4$, filtered, and evaporated. Flash chromatography of the crude mixture affords 1.26 g (80%) of N-methylthio compound (7, X=OMe, R=CCPh, R'=SMe): colorless solid; mp 74–76° C.; $^1$H NMR (400 MHz, CDCl$_3$) δ7.42 (d, J=8.8 Hz, 2H), 7.30 (m, 3H), 4.72 (d, J=4.8 Hz, 1H), 4.63 (d, J=4.8 Hz, 1H), 3.56 (s, 3H), 2.58 (s, 3H); $^{13}$C NMR (75 MHz, CDCl$_3$) δ169.8, 132.4, 129.6, 129.0, 122.5, 89.3, 86.6, 82.5, 59.0, 55.1, 22.7; IR (thin film) 1772 cm$^{-1}$ (β-lactam C═O). HRMS (CI, isobutane) calculated for C$_{13}$H$_{13}$NO$_2$S (M+1) 248.0742, obsd 248.0734. Anal. calculated for C$_{13}$H$_{13}$NO$_2$S: C, 63.13; H, 5.30. Found: C, 63.08; H, 5.33.

The following strains of bacteria were used to test β-lactam compounds for antimicrobial activity: *Escherichia coli* USF503 (ATCC 23590); *Enterobacter cloacae* USF510 (environmental isolate); *Salmonella typhimuriam* USF515 (obtained from the University of South Florida Medical Clinic); *Klebsiella pneumoniae* USF512; *Pseudomonas aeruginosa* USF620 (ATCC 15442); *Serratia marcescens* USF519 (ATCC29634); *Vibrio cholera* USF 1018 (biotype El Tor Inaba, cholera toxin positive, CDC E5906); *Vibrio cholera* USF 1019 (biotype El Tor Ogawa, cholera toxin negative, CDC1074-78); group B Streptococcus isolates 1211, 1212, 1220, 1224, 1233, and 5399; group A Streptococcus isolates 1, 122, 123, and 126; *Staphylococcus aureus* USF525 (ATCC 25923), and MRSA isolates 652–659. Bacteria were streaked for isolation onto tryptic soy agar (TSA) plates. An isolated colony from each plate was removed with a sterile swab and streaked onto a TSA plate. Sterile Bacto ¼-in. diameter concentration discs were impregnated with 20 μg of the test compound dissolved in 20 μL DMSO (or with DMSO, as a control), dried for three hours in a biohazard safety cabinet, and placed onto the inoculated TSA plates. The inoculated TSA plates with the compound-impregnated disks were incubated for about 24 hours at 37° C., and antimicrobial susceptibilities were determined by measuring the zone of growth inhibition around each disk, following the methods described by Bauer et al., *Am. J. Clin. Path.* 45:493 (1966).

Monocyclic β-lactam (3) was tested using the aforementioned methods and bacterial strains, and zones of growth inhibition were, where applicable, compared under identical conditions to zones of growth inhibition obtained using two standards, penicillin G and vancomycin. Strains for which penicillin G and vancomycin were not tested are marked "na" in the following tables. Diameters of zone inhibitions obtained using compound (3) and the two standards are shown in Table 1, which shows compound (3) to be an effective antibiotic, comparable in efficacy to the standards used in this test.

TABLE 1

Diameters of zone inhibition in mm

| Strain | Antibiotic/Antibacterial compound | | |
|---|---|---|---|
| | (3) | Penicillin G | Vancomycin |
| *E. coli* | 0 | na | na |
| *E. cloacae* | 0 | na | na |
| *T. salmonella* | 0 | na | na |
| *K. pneumonia* | 0 | na | na |
| *P. aeruginosa* | 0 | na | na |
| *S. marcescus* | 0 | na | na |
| *V. cholerae* 1018 | 0 | na | na |
| *V. cholerae* 1019 | 0 | na | na |
| Group B strep 1211 | 0 | na | na |
| Group B strep 1212 | 0 | na | na |
| Group B strep 1220 | 0 | na | na |
| Group B strep 1224 | 0 | na | na |
| Group B strep 1233 | 0 | na | na |
| Group B strep 5399 | 0 | na | na |
| Group A strep 1 | 0 | na | na |
| Group A strep 122 | 0 | na | na |
| Group A strep 123 | 0 | na | na |
| Group A strep 126 | 0 | na | na |
| *S. aureus* 525 | 10 | 38 | 28 |
| MRSA 652 | 0 | 8 | 23 |
| MRSA 653 | 15 | 15 | 20 |
| MRSA 654 | 9 | 9 | 20 |
| MRSA 655 | 10 | 13 | 19 |
| MRSA 656 | 12 | 10 | 20 |
| MRSA 657 | 12 | 12 | 21 |
| MRSA 658 | 10 | 18 | 20 |
| MRSA 659 | 0 | 16 | 20 |

EXAMPLE 2

In compounds (8) to (14), the N-methylthio group in lactam (3) is replaced by hydrogen (8), N-chloro (9), N-phenylseleno (10), N-methylsulfonamido (11), N-benzylthio (12), N-phenylthio (13), and a disulfide bonded analogue (14). Synthetic procedures similar to those described above for compound (3) may be used to synthesize these analogues of compound (3). Only replacement of the N-methylthio group (3) with N-benzylthio (12) produced a compound with detectable antibiotic activity. Among the bacterial strains tested, growth of *S. aureus* 525 is inhibited by compound (12), with a zone of inhibition of 3 mm. Therefore in the present invention, preferred R$_1$ or N-substituents are methylthio and benzylthio, while the most preferred β-lactam embodiments contain methylthio as the N-substituent at R$_1$.

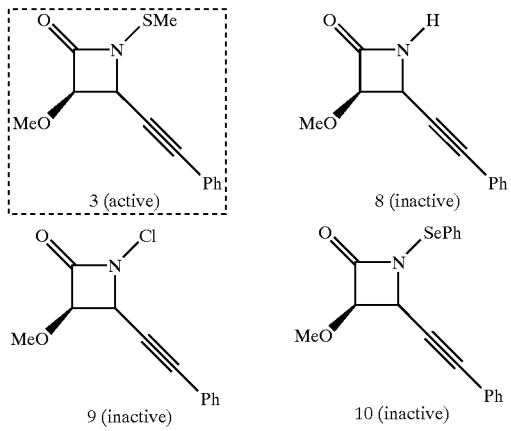

-continued

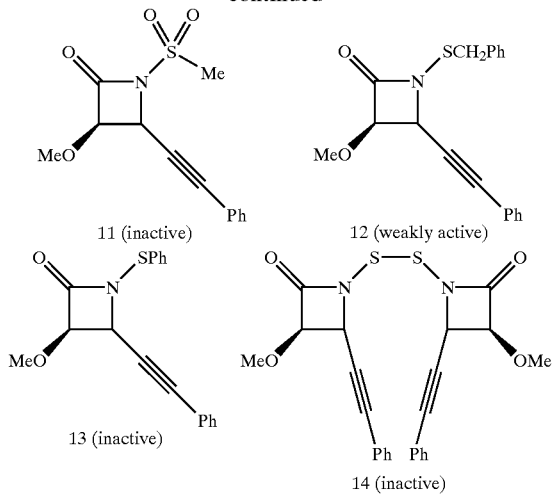

11 (inactive)
12 (weakly active)
13 (inactive)
14 (inactive)

EXAMPLE 3

Substitution of the methoxy group at $C_3$ of the ring to produce N-phthalimidyl derivative (15), benzylthio compound (16), and replacement of substituents at both $C_3$ and $C_4$ by hydrogen (17), yield non-bacteriocidal compounds. Therefore methoxy is preferred in the present invention at $C_3$, as bulkier substituents produced inactive compounds, as did removal of both the substituents at $C_3$ and $C_4$. However, the $C_4$ acetoxy-substituted β-lactam (18) has broad spectrum antibacterial activity, including against MRSA, as shown in Table 2:

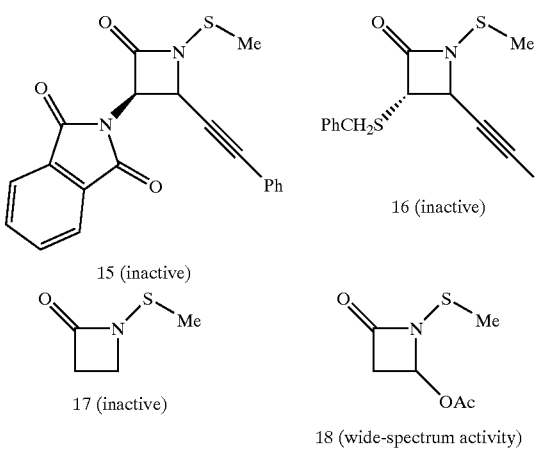

15 (inactive)
16 (inactive)
17 (inactive)
18 (wide-spectrum activity)

TABLE 2

Diameters of zone inhibition in mm

| | Antibiotic/Antibacterial compound | | |
|---|---|---|---|
| Strain | (18) | Penicillin G | Vancomycin |
| E. coli | 17 | na | na |
| E. cloacae | 15 | na | na |
| T. salmonella | 17 | na | na |
| K. pneumonia | 8 | na | na |
| P. aeruginosa | 12 | na | na |
| S. marcescus | 12 | na | na |
| V. cholerae 1018 | 20 | na | na |
| V. cholerae 1019 | 13 | na | na |
| Group B strep 1211 | 11 | na | na |
| Group B strep 1212 | 11 | na | na |
| Group B strep 1220 | 11 | na | na |
| Group B strep 1224 | 12 | na | na |
| Group B strep 1233 | 11 | na | na |
| Group B strep 5399 | 12 | na | na |
| Group A strep 1 | 11 | na | na |
| Group A strep 122 | 12 | na | na |
| Group A strep 123 | 11 | na | na |
| Group A strep 126 | 12 | na | na |
| S. aureus 525 | 18 | 38 | 28 |
| MRSA 652 | 15 | 8 | 23 |
| MRSA 653 | 12 | 15 | 20 |
| MRSA 654 | 9 | 9 | 20 |
| MRSA 655 | 16 | 13 | 19 |
| MRSA 656 | 18 | 10 | 20 |
| MRSA 657 | 20 | 12 | 21 |
| MRSA 658 | 17 | 18 | 20 |
| MRSA 659 | 16 | 16 | 20 |

Therefore in the present invention, preferred embodiments contain $C_3$ substituents of hydrogen or methoxy.

EXAMPLES 4–8

Substitution of N-thiolated β-lactam antibiotic (3) at the $C_4$ position with a variety of substituents produces active antibacterial compounds in the alkenyl derivative (19), ortho-chlorophenyl derivative (20), ortho-nitrophenyl derivative (21), and 2-thiophene derivatives (22) and (23). In contrast, compounds (25) to (27) are inactive, illustrating how slight structural differences, such as for example between ortho- and meta-nitro substitution in compounds (21) and (25), respectively, are important in determining antibacterial properties in the present invention.

TABLE 3

Diameters of zone inhibition in mm

| | Antibiotic/Antibacterial compound | | | | | | | |
|---|---|---|---|---|---|---|---|---|
| Strain | (19) | (20) | (21) | (22) | (23) | (24) | Penicillin G | Vancomycin |
| E. coli | 0 | 0 | 0 | 0 | 0 | 0 | na | na |
| E. cloacae | 0 | 0 | 0 | 0 | 0 | 0 | na | na |
| T. salmonella | 0 | 0 | 0 | 0 | 0 | 0 | na | na |

TABLE 3-continued

Diameters of zone inhibition in mm

| | Antibiotic/Antibacterial compound | | | | | | | |
|---|---|---|---|---|---|---|---|---|
| Strain | (19) | (20) | (21) | (22) | (23) | (24) | Penicillin G | Vancomycin |
| K. pneumonia | 0 | 0 | 0 | 0 | 0 | 0 | na | na |
| P. aeruginosa | 0 | 0 | 0 | 0 | 0 | 0 | na | na |
| S. marcescus | 0 | 0 | 0 | 0 | 0 | 0 | na | na |
| V. cholerae 1018 | 0 | 0 | 0 | 0 | 0 | 0 | na | na |
| V. cholerae 1019 | 0 | 0 | 0 | 0 | 0 | 0 | na | na |
| Group B strep 1211 | 0 | 0 | 0 | 0 | 0 | 0 | na | na |
| Group B strep 1212 | 0 | 0 | 0 | 0 | 0 | 0 | na | na |
| Group B strep 1220 | 0 | 0 | 0 | 0 | 0 | 0 | na | na |
| Group B strep 1224 | 0 | 0 | 0 | 0 | 0 | 0 | na | na |
| Group B strep 1233 | 0 | 0 | 0 | 0 | 0 | 0 | na | na |
| Group B strep 5399 | 0 | 0 | 0 | 0 | 0 | 0 | na | na |
| Group A strep 1 | 0 | 0 | 0 | 0 | 0 | 0 | na | na |
| Group A strep 122 | 0 | 0 | 0 | 0 | 0 | 0 | na | na |
| Group A strep 123 | 0 | 0 | 0 | 0 | 0 | 0 | na | na |
| Group A strep 126 | 0 | 0 | 0 | 0 | 0 | 0 | na | na |
| S. aureus 525 | 16 | 28 | 12 | 15 | 18 | 27 | 38 | 28 |
| MRSA 652 | 12 | 25 | 14 | 13 | 17 | 26 | 8 | 23 |
| MRSA 653 | 15 | 27 | 12 | 20 | 18 | 28 | 15 | 20 |
| MRSA 654 | 14 | 26 | 11 | 17 | 16 | 25 | 9 | 20 |
| MRSA 655 | 11 | 24 | 14 | 15 | 13 | 26 | 13 | 19 |
| MRSA 656 | 13 | 23 | 15 | 17 | 15 | 24 | 10 | 20 |
| MRSA 657 | 15 | 27 | 12 | 16 | 17 | 29 | 12 | 21 |
| MRSA 658 | 12 | 20 | 16 | 17 | 18 | 22 | 18 | 20 |
| MRSA 659 | 18 | 24 | 15 | 13 | 20 | 26 | 16 | 20 |

EXAMPLES 9–11

Certain compounds of the present invention have antibacterial activity directed against the bacterial species responsible for the disease gonorrhea, which is *Neisseria Gonorrhoeae*. Zones of inhibition for compounds of the present invention are measured using the aforementioned methods, and according to the method described be Bauer, et al., (1966) *Am. J. Clin. Path.* 45:493, using a beta-lactamase producing strain of *Neisseria Gonorrhoeae*. N-1 thiolated monobactams (20), (24), (28), (29), and (30), all produce substantial zones of growth inhibition (measured in mm), with the values as shown below each chemical structure herein. Gonorrhea is a prevalent bacterial disease that is increasingly resistant to existing antibiotics. Synthesis of new antibacterials and antibiotics according to the present invention may therefore be extremely useful in the control of gonorrhea and similar bacterial diseases.

Publications cited throughout this document are each herein incorporated by reference in their respective entireties.

While the invention has been described in terms of various preferred embodiments, those skilled in the art will recognize that various modifications, substitutions, omissions, and changes may be made without departing from the spirit of the present invention. Accordingly, it is intended that the scope of the present invention be limited solely by the scope of the following claims.

What is claimed is:

1. A monocyclic β-lactam compound of the formula:

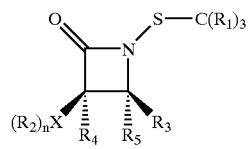

or a salt or hydrate thereof, wherein:

—C(R$_1$)$_3$ is methyl, ethyl, —CH$_2$Ph or benzyl;

—X(R$_2$)$_n$ is methoxy, hydrogen, or X(R$_2$)$_n$ and R$_4$ forms a spirocycle R$_3$ is acetyl, aryl, heteroaryl, aryl(C$_1$–C$_6$)alkyl, heteroaryl(C$_1$–C$_6$)alkyl, aryl(C$_2$–C$_6$)alkenyl, heteroaryl(C$_2$–C$_6$)alkenyl, aryl(C$_2$–C$_6$)alkynyl or heteroaryl(C$_2$–C$_6$)alkynyl; wherein any aryl or heteroaryl is optionally substituted with halo, nitro, cyano, hydroxy, trifluoromethyl, trifluoromethoxy, (C$_1$–C$_{15}$)alkyl, (C$_2$–C$_{15}$)alkenyl, (C$_2$–C$_{15}$)alkynyl, (C$_3$–C$_8$)cycloalkyl, (C$_3$–C$_8$)cycloalkyl(C$_1$–C$_{15}$)alkyl, (C$_3$–C$_8$)cycloalkyl-C$_2$–C$_{15}$)alkenyl, (C$_3$–C$_8$)cycloalkyl(C$_2$–C$_{15}$)alkynyl, (C$_1$–C$_{15}$)alkoxy, (C$_1$–C$_{15}$)alkanoyl, (C$_1$–C$_{15}$)alkanoyloxy, C(O)O(C$_1$–C$_6$)alkyl, C(=O)N((C$_1$–C$_6$)alkyl)$_2$, or N((C$_1$–C$_6$)alkyl)$_2$;

R$_4$ is hydrogen, or X(R$_2$)$_n$ and R$_4$ forms a spirocycle;

R$_5$ is hydrogen; and excluding the compounds 1-thiomethyl-3-methoxy-4-phenylethynyl-2-oxoazetidine, and 1-thiomethyl-3-methoxy-4-(O-acetyl)phenylethynyl-2oxoazetidine.

2. The compound of claim 1, wherein R$_4$ and R$_5$ are hydrogen.

3. The compound of claim 2, wherein —C(R$_1$)$_3$ is methyl, —X(R$_2$)$_n$ is methoxy, and R$_3$ is phenylethynyl.

4. The compound of claim 2, wherein —C(R$_1$)$_3$ is —CH$_2$Ph, —X(R$_2$)n is methoxy, and R$_3$ is phenylethynyl.

5. The compound of claim 2, wherein —C(R$_1$)$_3$ is methyl, —X(R$_2$)$_n$ is hydrogen, and R$_3$ is acetyl.

6. The compound of claim 2, wherein —C(R$_1$)$_3$ is methyl, —X(R$_2$)$_n$ is methoxy, and R$_3$ is ortho-chlorophenyl.

7. The compound of claim 2, wherein —C(R$_1$)$_3$ is methyl, —X(R$_2$)$_n$ is methoxy, and R$_3$ is ortho-nitrophenyl.

8. The compound of claim 2, wherein —C(R$_1$)$_3$ is methyl, —X(R$_2$)$_n$ is methoxy, and R$_3$ is 2-thiophene.

9. The compound of claim 2, wherein —C(R$_1$)$_3$ is methyl, —X(R$_2$)$_n$ is methoxy, and R$_3$ is S,S-dioxo-thiophene.

10. The compound of claim 2, wherein —C(R$_1$)$_3$ is methyl, —X(R$_2$)$_n$ is methoxy, and R$_3$ is para-chlorophenyl.

11. The compound of claim 2, wherein —C(R$_1$)$_3$ is methyl, —X(R$_2$)$_n$ is methoxy, and R$_3$ is meta-chlorophenyl.

12. The compound of claim 2, wherein —C(R$_1$)$_3$ is methyl, —X(R$_2$)$_n$ is methoxy, and R$_3$ is ortho-chlorophenyl.

13. The compound of claim 2, wherein —C(R$_1$)$_3$ is methyl, —X(R$_2$)$_n$ is methoxy, and R$_3$ is phenyl.

14. The compound of claim 1, wherein R$_3$ is phenyl, phenylethynyl, orthochlorophenyl, ortho-nitrophenyl, 2-thiophene, S,S-dioxo-thiophene; para-chlorophenyl, meta-chlorophenyl, para-chlorophenyl, or aryl substituted with —C(O)O(C$_1$–C$_6$)alkyl.

15. A monocyclic β-lactam compound selected from the group consisting of:

16. A composition comprising an N-1 thiolated monocyclic β-lactam, or a salt or hydrate thereof, in a pharmaceutically acceptable carrier.

17. A composition comprising a compound of claim 1, in a pharmaceutically acceptable carrier.

18. A method for inhibiting growth of a bacterium, comprising administering to said bacterium an effective amount of an N-1 thiolated monocyclic β-lactam, or a salt of a hydrate thereof.

19. A method of treating a patient having a bacterial infection, said method comprising administering to said patient at least one dose of an effective amount of the composition of claim 16.

20. The method of claim 19, wherein said bacterial infection is gonorrhea.

\* \* \* \* \*

UNITED STATES PATENT AND TRADEMARK OFFICE
CERTIFICATE OF CORRECTION

PATENT NO. : 6,476,015 B1
DATED : November 5, 2002
INVENTOR(S) : Edward Turos et al.

It is certified that error appears in the above-identified patent and that said Letters Patent is hereby corrected as shown below:

Column 1,
Line 40, "Lactum" should read -- Lactam --.

Column 5,
Line 47, "($C_1$-$C_{15}$)" should read -- ($C_1$-$C_{15}$) --.

Column 6,
Line 7, "$C_3$-$C_8$)" should read -- ($C_3$-$C_8$) --.

Column 14,
Line 55, "in the present invention.

TABLE 3"

should read -- in the present invention.

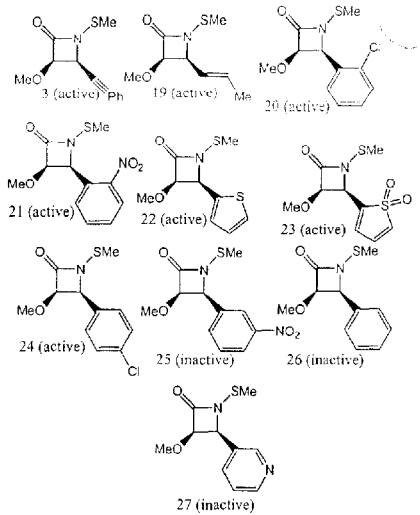

TABLE 3--

UNITED STATES PATENT AND TRADEMARK OFFICE
CERTIFICATE OF CORRECTION

PATENT NO.   : 6,476,015 B1
DATED        : November 5, 2002
INVENTOR(S)  : Edward Turos et al.

It is certified that error appears in the above-identified patent and that said Letters Patent is hereby corrected as shown below:

Column 17,
Line 11, "group consisting of:" should read -- group consisting of:

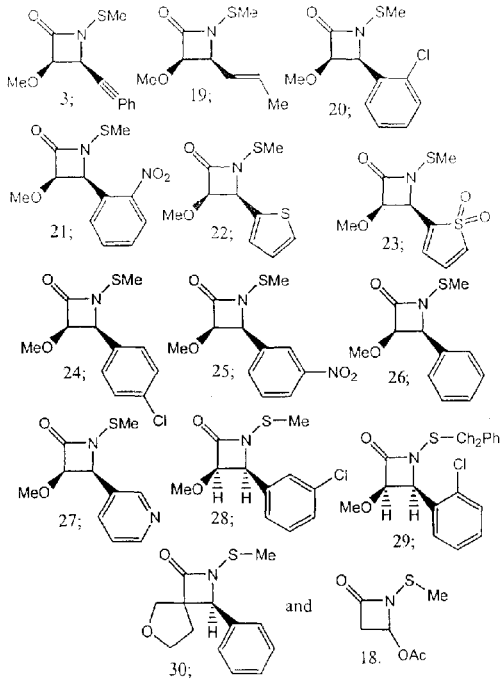

--

Signed and Sealed this

Sixth Day of January 2004

JAMES E. ROGAN
*Director of the United States Patent and Trademark Office*